United States Patent [19]

Loe

[11] 4,064,908
[45] Dec. 27, 1977

[54] COMBINATION NEEDLE FLOW CONTROL AND SHUT-OFF VALVE FOR PRECISION INSTRUMENTS

[76] Inventor: Winston C. Loe, 4851 Del Monte Road, La Canada, Calif. 91011

[21] Appl. No.: 673,753

[22] Filed: Apr. 5, 1976

[51] Int. Cl.² ............................................. F16K 1/04
[52] U.S. Cl. ............................ 137/614.17; 251/122
[58] Field of Search ..................... 137/614.17, 599.2; 251/121, 122

[56] References Cited
U.S. PATENT DOCUMENTS

| 916,163 | 3/1909 | Jettinger | 137/614.17 |
|---|---|---|---|
| 1,527,358 | 2/1925 | Hamilton | 137/599.2 |
| 2,791,236 | 5/1957 | Mauer | 137/614.17 X |
| 3,117,595 | 1/1964 | Broecker et al. | 137/614.17 X |
| 3,870,080 | 3/1975 | Landwehr | 137/614.17 X |

FOREIGN PATENT DOCUMENTS

| 1,115,243 | 12/1955 | France | 137/614.17 |
|---|---|---|---|
| 641,803 | 4/1928 | France | 137/599.2 |

Primary Examiner—Robert G. Nilson
Attorney, Agent, or Firm—Robert C. Comstock

[57] ABSTRACT

A combination flow control and shut-off valve comprising a body having an elongated opening with separated inlet and outlet passages. An elongated valve cartridge is screw threadedly mounted for longitudinal movement within said opening to open and close the connection between the inlet and outlet passages. An elongated needle member is screw threadedly mounted within the valve cartridge and is rotatable to move an elongated tapered needle longitudinally within a cylindrical opening formed in the valve cartridge for precisely controlling the flow of fluid between the inlet and outlet passages. The cartridge is movable independently from the needle member to turn the flow of fluid through the valve completely on and off without affecting the precision flow control setting of the needle.

8 Claims, 4 Drawing Figures

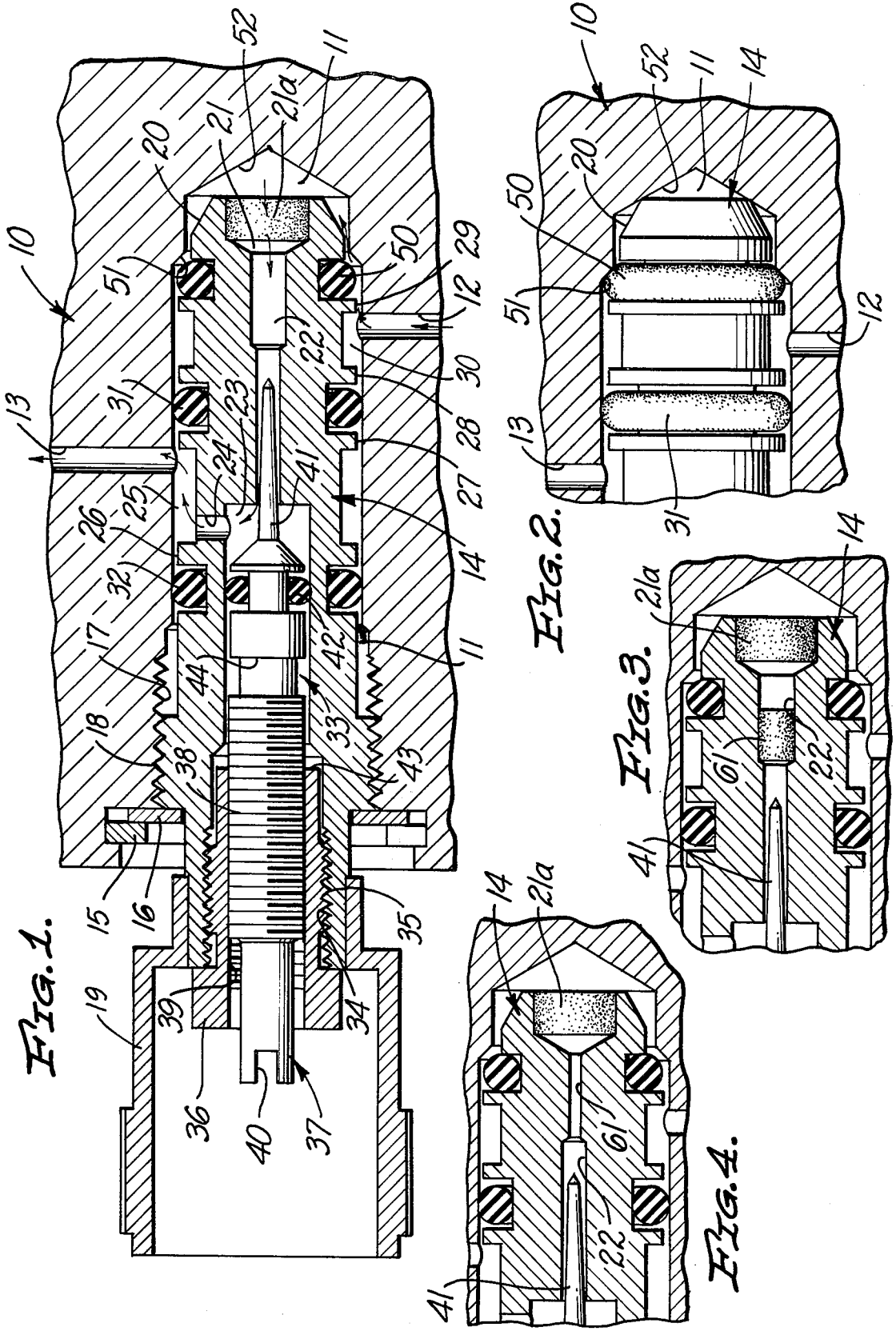

COMBINATION NEEDLE FLOW CONTROL AND SHUT-OFF VALVE FOR PRECISION INSTRUMENTS

BACKGROUND OF THE INVENTION

1. Field of the Invention

The invention relates to a combination needle type precision flow control valve and shut-off valve for gas chromatographs and other precision instruments.

2. Description of the Prior Art

In gas chromatography and other types of precision instrumentation, a needle type valve is frequently used to control the flow of fluids. Because of the extremely small area through which the fluid passes, precise adjustment of the needle valve setting to the flow desired is critical for proper operation of the instrument. This adjustment often requires a considerable amount of time and extreme care to achieve.

At the present time, this precision setting is completely lost whenever the valve is shut off and it requires time and painstaking effort to reset the needle valve to the desired adjustment.

SUMMARY OF THE INVENTION

In essence, the present invention contemplates a needle type precision flow control valve which is movably mounted concentrically within a valve cartridge, which is in turn movably mounted within a stationary valve body. The needle type valve is movable to adjust and control the flow of fluid through the valve, while the valve cartridge is movable to open and close the flow which is controlled by the needle valve.

A primary object of the present invention is to provide a precision needle type flow control valve in combination with a shut-off valve in which the valve can be moved between open and closed position without in any way changing or affecting the setting of the needle flow control valve.

The device is particularly adapted for use in gas chromatographs for adjusting and controlling the flow of hydrogen, air, carrier gas, etc. It may also be used as a flow restriction element in hydraulic, pneumatic and other systems. The device is also capable of use in other types of precision instruments in which precise flow control is desired along with shutoff capability without disturbing the flow control setting.

Another object of the invention is to provide a single valve assembly which serves a dual purpose. The combination valve of the present invention eliminates the necessity for using the needle valve as a shut-off valve or for providing a separate shut-off valve elsewhere in the system.

A more particular object of the invention is to provide a device of the type described in which screw threading is utilized to provide a mechanical advantage to work against the substantial pressure to which the valve is subjected. Without this mechanical advantage, it would be necessary to provide an elaborate balanced seal arrangement in order to withstand the pressure. If a push-pull type of construction were utilized, additional O-ring seals would be required for a balanced configuration. A rotary shut-off would require a more elaborate and expensive valve construction.

The screw threading is also utilized to serve a further function of making the valve assembly and its component parts accessible from the front panel of the instrument, thereby making repairs and replacements simple and avoiding complex and time consuming repair operations.

Another object of the invention is to provide a device of the type described in which the fluid flow through the valve can be moved between fully open and fully closed positions with only a single rotation of the on-off control knob.

It is accordingly among the objects of the invention to provide a combination valve of the type described which has the advantages and benefits set forth above and described in further detail hereinafter in this specification.

A further object of the invention is to provide such a valve which is simpler and more economical to manufacture and use than existing valves which perform the same or similar function.

The invention also comprises such other objects, advantages and capabilities as will later more fully appear and which are inherently possessed by the invention.

While there is shown in the accompanying drawings a preferred embodiment of the invention, it should be understood that the same is susceptible of modification and change without departing from the spirit of the invention.

DESCRIPTION OF THE DRAWINGS

FIG. 1 is a longitudinal sectional view of the valve assembly with the needle valve and shut-off valve both in open position;

FIG. 2 is a similar partial sectional view with the shut-off valve in closed position;

FIG. 3 is a partial sectional view of an alternative embodiment of the invention in which a sintered metal slug is used to reduce pressure in the needle area;

FIG. 4 is a partial sectional view of another alternative embodiment of the invention in which a passage of reduced diameter is used to reduce pressure in the needle area.

DESCRIPTION OF THE PREFERRED EMBODIMENT

A preferred embodiment which has been selected to illustrate the invention comprises a combination valve having a stationary body 10, which may comprise a separate member or an integral part of the instrument with which the valve is used.

The body 10 is provided with an elongated longitudinally directed opening 11. Extending transversely to the opening 11 and connecting therewith are a lower inlet passage 12 and an upper outlet passage 13.

An elongated valve cartridge 14 is removably mounted within the opening 11, being held therein by a split ring retainer 15 which is disposed within a recess formed adjacent to the outer end of the opening 11. A washer 16 is disposed between the retainer 15 and the adjacent portion of the body 10.

The outer end of the opening 11 is provided with internal screw threading 17 which engages external screw threading 18 formed on the outer portion of the cartridge 14. An on-off control knob 19 is fixedly secured to the outer end of the cartridge 14. Rotation of the knob 19 causes rotation of the cartridge 14 to move it longitudinally toward or away from the inner end of the opening 11.

The valve cartridge 14 is provided with a tapered inner end 20 having an inlet 21 within which is mounted a sintered metal filter 21a. The inlet 21 is connected to a passage 22 which extends along the longitudinal axis of the cartridge 14 to a chamber 23, which is in turn connected to a transversely directed outlet 24. The outlet 24 is in turn connected to a movable chamber 25 which surrounds the cartridge 14 and which is connected with the outlet passage 13 of the body 10.

The chamber 25 is defined longitudinally by a pair of outwardly projecting rings 26 and 27 which extend around the cartridge 14 and which are formed integrally therewith. A second pair of similarly formed rings 28 and 29 define a second movable chamber 30 which surrounds the cartridge 14 and which is connected with the inlet passage 12 of the body 10.

A resilient O-ring 31 is mounted between the rings 27 and 28 to provide a fluid tight seal between the cartridge 14 and the body 10. The O-ring 31 prevents leakage from the high pressure (inner) side to the low pressure (outer) side of the cartridge 14.

Anothr O-ring 32 is mounted between the ring 26 and an adjacent portion of the cartridge 14. The O-ring 32 prevents leakage from the low pressure side of the cartridge 14 to the outside or atmosphere through the outer end of the cartridge 14. Both of the O-rings 31 and 32 form moving seals with the inner wall of the opening 11.

The cartridge 14 is provided with an axial opening 33 which extends continuously from the outer end of the cartridge 14 to the passage 22, with the chamber 23 comprising the inner end portion of the axial opening 33.

The outer end of the opening 33 is provided with internal screw threading 34 which threadedly engages external screw threading 35 formed on the outside of the shank of an elongated needle retainer 36. The needle retainer 36 has an enlarged head, the inner end of which fits against the outer end of the cartridge 14.

An elongated needle member 37 is movably mounted with the axial opening 33. The outer end of the needle member 37 is provided with external screw threading 38 which engages internal threading 39 formed on the needle retainer 36. The outer end of the needle member 37 is provided with a transverse slot 40 which is adapted to receive the blade of a screw driver to rotate the needle member 37 and thereby move it longitudinally within the opening 33.

The inner end of the needle member 37 comprises an integral elongated tapered needle 41, which extends into the outer end of the passage 22 in the cartridge 14. The clearance between the outer surface of the needle 41 and the adjacent inner surface of the passage 22 may be extremely small, as may the taper of the needle 41 for very fine flow adjustment of low flow rates. However, the passage size and needle taper may be selected to cover a wide range of flow rate requirements.

The needle 41 may alternatively comprise a cylindrical pin with a tapered slice removed from one side thereof.

The inner portion of the needle member 37 is provided with an O-ring 42 which forms a seal with the adjacent wall of the opening 33. The O-ring 42 prevents leakage from the chamber 23 outwardly through the opening 33.

The inner end of the needle retainer 37 is provided with a flat face 43 which is adapted to engage a flat face 44 formed on the needle member 37 to limit outward movement of the needle member 37. Inward movement of the needle member 37 is limited by engagement of the needle 41 with the passage 22 and/or by engagement between the portion of the needle member adjacent to the outer end of the needle 41 and the radial wall defining the inner end of the opening 33 and chamber 23.

Surrounding the inner end of the cartridge 14 is an O-ring 50 which upon inward movement of the cartridge 14 is adapted to make sealing engagement with an inwardly tapered wall 51 disposed adjacent to the inner end of the opening 11. Inward movement of the cartridge 14 within the opening 11 may be limited by this engagement and/or by engagement between the inner end of the cartridge 14 and an inwardly tapered wall 52 which defines the inner end of the opening 11.

The O-ring 50 is closed sealing position may be moved in whole or in part beyond the inner edge of the wall 51 into the portion of the opening 11 adjacent to the inner end of the wall 51.

Referring to FIG. 1, which shows the valve in open position, fluid pressure flows through the inlet passage 12 past the O-ring 50 into the inner end of the opening 11. It then flows through the inlet 21 and filter 21a and through the passage 22 around the needle 41 into the chamber 23. The fluid then flows through the outlet opening 24 and the movable chamber 25 outwardly through the outlet passage 13.

The amount of flow is controlled by rotational adjustment of the longitudinal position of the needle member 37 within the outer end of the passage 22 in the cartridge 14 through use of a screw driver disposed in the slot 40. As the needle member 37 is moved inwardly, it reduces flow by diminishing the passage between the needle 41 and the adjacent wall of the passage 22. Outward movement of the needle 41 increases the clearance and thereby increases the flow.

The needle 41 provides extremely precise control of the fluid flow. Once it has been set, its setting need not be changed or disturbed in order to start or stop the flow of fluid through the valve. This is accomplished through manual rotation of the knob 19, which moves the cartridge 14 inwardly within the opening 11 until the O-ring 50 engages the wall 51 to prevent any further flow of fluid between the inlet passage 12 and the inlet 21 of the cartridge 14. Rotation of the knob 19 in the opposite direction opens the valve for operation. Both opening and closing of the fluid flow are achieved without affecting the setting of the needle 41.

The device is preferably constructed and arranged so that only a single rotation of the knob 19 is required to move the cartridge 14 between fully open and fully closed positions.

In order to provide more precise and more easily controlled flow adjustment, it may be necessary or desirable to reduce the amount of pressure in the area of the needle 41 and passage 22. This may be accomplished by inserting an additional sintered metal slug 61 between the filter 21a and the tip of the needle 41, and as shown in FIG. 3 of the drawings.

It may also be achieved by pressing or machining a passage 61 of reduced diameter between the filter 21a and the tip of the needle 41, as shown in FIG. 4 of the drawings.

In either case, the flow is restricted in order to provide easier and finer flow adjustment. If excessive pressure is not restricted, a slight change in the needle position will result in a large change in flow, so that fine flow control is difficult to achieve.

I claim:

1. A combination needle flow control and shut-off valve for precision instruments comprising a body, an elongated opening formed within said body, separated inlet and outlet passages connected with said opening, an elongated cartridge screw threadedly mounted in said body opening for longitudinal movement within said opening to open and close the connection between said inlet and outlet passages, said cartridge having an opening therein connecting said inlet and outlet passages when said cartridge is disposed in open position, an elongated needle member screw threadedly mounted within said cartridge for longitudinal movement within said cartridge, said needle member having a tapered needle longitudinally movable within said opening in said cartridge for precisely controlling the flow of fluid between said inlet and outlet passages, means connected to the outer ends of said cartridge and needle member for rotating and longitudinally moving said members independently from each other, so that said cartridge may be moved between open and closed positions to turn the flow of fluid through the valve completely on and off without affecting the precision flow control setting of said needle, an O-ring mounted adjacent to the end of said cartridge surrounding said cartridge, an inwardly extending portion of said body disposed adjacent to said O-ring, said O-ring being adapted to be compressed into sealing engagement with said inwardly extending portion of said body upon inward movement of said cartridge to close off the connection between said inlet passage and said outlet passage, said cartridge having an inner end engageable with the inner end of said body opening after said O-ring has made sealing engagement with said body to limit further inward movement of said cartridge.

2. The structure described in claim 1, and a porous flow restricting member disposed between said inlet passage and said needle to provide easier and finer flow control upon movement of said needle.

3. The structure described in claim 1, and a pair of O-rings surrounding said cartridge and making continuous moving sealing engagement with the inner surface of said body opening to prevent the leakage of fluid from said inlet passage to said outlet passage and from said passages to the atmosphere.

4. The structure described in claim 3, said needle member being screw threadedly mounted in a needle retainer, said needle retainer being screw threadedly mounted in a fixed position between said cartridge and said body.

5. The structure described in claim 4, said needle retainer having a radial wall disposed adjacent to the inner end thereof, said needle member having a radial wall formed on the midportion thereof, said radial walls being engageable with each other to limit the outward movement of said needle member.

6. The structure described in claim 5, and a control knob mounted within the outer end of said cartridge for controlling the rotation of said cartridge, said control knob having a hollow interior, the outer end of said needle member being disposed within said hollow interior and having means thereon for removably receiving a driver member to control the rotation of said needle member.

7. The structure described in claim 6, said valve cartridge, needle retainer and needle member all being removable through the outer end of said body opening.

8. The structure described in claim 1, and a porous filter carried by the inner end of said cartridge, said cartridge being removable from said body for cleaning or replacing said filter.

* * * * *